United States Patent [19]

Murdock

[11] Patent Number: 4,608,998
[45] Date of Patent: Sep. 2, 1986

[54] KNEE ALIGNMENT MONITORING APPARATUS

[75] Inventor: Wilbert Murdock, New York, N.Y.

[73] Assignee: COM Sports, Inc., New York, N.Y.

[21] Appl. No.: 561,681

[22] Filed: Dec. 15, 1983

[51] Int. Cl.$^4$ ............................................. A61B 5/10
[52] U.S. Cl. .................................... 128/782; 340/573
[58] Field of Search ................. 128/774, 782; 340/573

[56] References Cited

U.S. PATENT DOCUMENTS

| | | | |
|---|---|---|---|
| 3,642,276 | 2/1972 | Kropf | 128/782 X |
| 4,306,571 | 12/1981 | McLeod | 128/782 |
| 4,444,205 | 4/1984 | Jackson | 128/774 X |

FOREIGN PATENT DOCUMENTS

| | | | |
|---|---|---|---|
| 2848396 | 5/1980 | Fed. Rep. of Germany | 128/774 |
| 0578061 | 10/1977 | U.S.S.R. | 128/782 |
| 0880407 | 11/1981 | U.S.S.R. | 128/782 |

OTHER PUBLICATIONS

Endicott et al., Med. and Biol. Engr., vol. 12, No. 3, May 1974.
Johnson et al., Med. and Biol. Eng. and Comput., vol. 19, No. 2, Mar. 1981, pp. 255-256.
Foster et al., Med. Res. Eng., vol. 13, No. 2, 1980, pp. 17-21.
Johnson et al., Med. and Biol. Eng. and Comput., vol. 17, 1979, pp. 145-154.

*Primary Examiner*—Kyle L. Howell
*Assistant Examiner*—John C. Hanley
*Attorney, Agent, or Firm*—Arthur L. Plevy

[57] ABSTRACT

A knee alignment device employing a plurality of sensors which are positioned about various areas of a user's knee. The sensors are coupled to circuitry including a microprocessor which has stored therein optimum values indicating correct knee motion during an exercise. These values are compared with the actual values being generated by a user in performing the same exercise, and if the actual values exceed those stored in the microprocessor, the user is warned of a dangerous condition which is indicative in informing him to modify the exercise being performed.

18 Claims, 6 Drawing Figures

KNEE ALIGNMENT MONITORING APPARATUS

BACKGROUND OF THE INVENTION

This invention relates to an apparatus for monitoring the force at a joint of the human body and more particularly for monitoring forces of a knee joint associated with the human body.

As can be ascertained, a great deal of injuries are suffered by atheletes and various other individuals regarding the knee joint.

The knee joint as known is found between two of the longest bones in the body; namely, the femur and the tibia. In regard to this the amount of leverage which can be brought to bear upon the joint is extremely large and is, or course, a function of the size and weight of the individual. The knee joint also exhibits a relatively complicated pattern of motion and essentially consists of three articulations in one.

Based on the degree of motions, the articulation of the knee joint is relatively insecure, but because of the very powerful ligaments which bind the bones together, the joint is one of the strongest in the body. Essentially, if the ligaments have been softened or destroyed by accident or disease, partial displacement of the knee joint is a common occurrence. This can be brought about by the action of the body muscles displacing the articular surfaces from each other. Hence in regard to this the tibia may be disclocated in any direction from the femur resulting in injury to the knee joint.

The directions can be forward, backward, inward, or outward or a conbination of two of these dislocations may occur. In regard to this the tibia may be dislocated forward and laterally, or backward and laterally and any of these dislocations may be complete or incomplete. There are other injuries which can occur in regard to cartilage injuries which cartilages can become displaced and captured between the femur and tibia.

These type of accidents are produced by a twist of the leg when the knee is flexed and are accompanied by pain and fixation of the knee in a flex position. The cartilage may be displaced either inward or outward.

As one can ascertain, the injuries which can occur to the knee are extensive and extremely debilitating. Based on modern medical practices, most of the conditions can be alleviated by surgery or various forms of therapy. In any event, it is well known that based on body type and size and activity engaged in, any injury can occur in different individuals due to different factors, and hence the cause of such injuries is extremely complicated. It is a particular object of the present invention to provide a device which can be employed by individuals such as atheletes to allow them to determine whether the knee is properly aligned during an exercise which device will monitor the proper knee alignment for the particular individual and will indicate to the individual via a display or otherwise when the knee joint is not properly aligned or is subjected to extreme forces which may result in an injury.

In this manner the individual or athelete is continuously advised by the apparatus as to whether or not the particular exercise may result in injury, and therefore, the individual is able to modify the exercise according to the information received from the apparatus. It is, of course, understood that the apparatus can also be employed by persons who have already injured their knee joints and are in the process of recuperating in order to strengthen the joint so that they may engage in future activities.

These and other objects of the present invention will become apparent in regard to the following specification.

BRIEF DESCRIPTION OF THE PREFERRED EMBODIMENT

Apparatus for monitoring the proper alignment of a knee of a user, comprising transducer means coupled to the knee of said user and operative to provide an output signal indicative of the relative forces on the knee joint during an exercise, memory means having stored therein data indicative of proper force levels for said knee during said exercise, comparison means operative to compare said stored data with said output signal to provide an indication when said output signal exceeds said stored data signal, and means responsive to said indication to provide a warning to said user according to the generation of said indication.

DETAILED DESCRIPTION OF THE FIGURES

Figure 1:
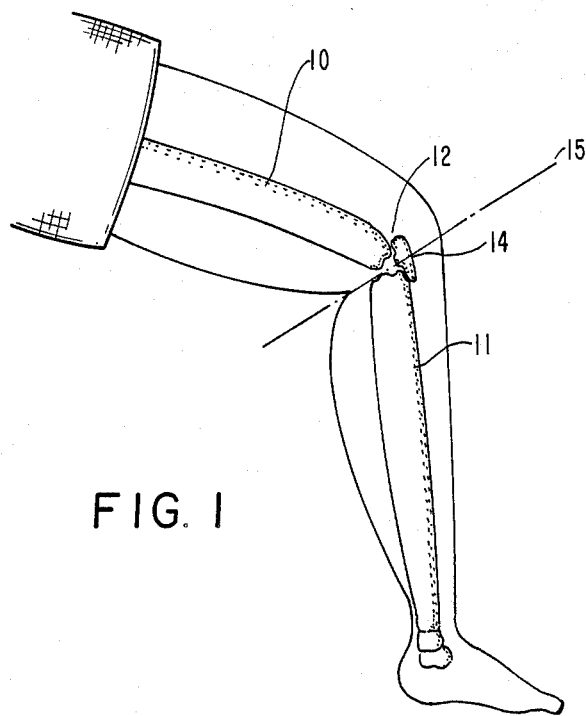
FIG. 1 is an anatomical view depicting the knee joint.

Referring to FIG. 1, there is shown a simple anatomical diagram of the knee and the knee joint in order to clearly explain the present invention.

As indicated, the knee joint is located between the two largest bones in the body; namely, the femur 10 and the tibia 11. The knee joint 12 basically consists of a series of external and interior ligaments which connect the femur and the tibia together. The bones entering into the formation of the knee joint 12 are the condyles of the femur above, the head of the tibia below and the patella 14 in front.

These bones, as indicated, are connected together by ligaments, some of which are placed on the exterior of the joint, while others occupy its interior. As indicated, the articulations and motions of the knee joint are well known in the medical field.

As shown in FIG. 1, there is a dashed line 15 which essentially is drawn through the center of the knee joint or the space between the femur and tibia.

The various forces exerted on the bones during a course of exercise essentially determines the resultant or net force exerted at the knee joint. It is, of course, understood that the actual magnitude of the force is of no consequence as it is a function of the individual based on body exercise and weight as indicated above and also based on the flexibility and condition of the ligaments of the individual as well as his age and so on.

The present invention, as will be described, serves to operate by detecting the difference or magnitude of force at the area of the tibia with respect to the femur to thereby obtain a voltage or signal which is proportional to the effect or force on the knee as well as the actual motion in regard to rotation or flexure of the knee which essentially provides a signal which is proportional to the displacement of the tibia with respect to the femur or vice versa.

This displacement can be detected in a vertical, horizontal or angular direction as will be explained.

Figure 2:
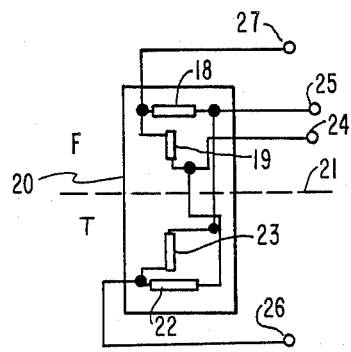
FIG. 2 is a top plan view of a transducer employed in this invention.

Referring to FIG. 2, there is shown one type of transducer which can be employed in the present invention.

Figure 3:
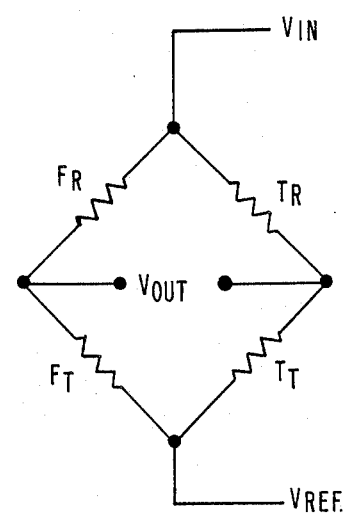
FIG. 3 is a schematic view of a Wheatstone bridge array.

Essentially, numeral 20 references a planar thin flexible plastic layer which has deposited thereon variable resistive devices as 18, 19, 22, and 23. These devices may be piezoresistors or other variable resistor devices which change resistance in response to an applied force or pressure to the flexible diaphragm 20. There are many other types of variable resistors which can be employed as well. The variable resistive devices as 18, 19, 22 and 23 are positioned on the thin diaphragm 20 in pairs with two resistors as 18 and 19 responsive to forces exerted on the femure (F) and two resistors as 22 and 23 responsive to forces on the tibia (T). In this manner the resistors as shown are positioned above and below the center line 21 which corresponds to the center line 15 of the knee joint as shown in FIG. 1. The resistors are wired on the substrate to form a Wheatstone bridge array as shown in FIG. 3. The resistors are positioned on the substrate so that one resistor in each pair responds to radial stress, while the other resistor in each pair responds to tangential stress.

As shown in FIG. 3, a Wheatstone bridge array is formed with the femur resistors in one arm of the bridge and the tibia resistors in the other arm of the bridge. The lead designated VIN which is lead 25 of FIG. 2 is connected to a biasing source, while the lead designated VREF is a reference potential lead and shown in FIG. 2 as 24. The output is taken via the junction leads between the resistors as lead 27 for the F transducer and lead 26 for the T transducer.

Figure 4:
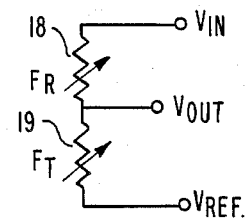
FIG. 4 is a schematic view depicting two variable resistors used in this invention.

As shown in FIG. 4, each transducer may be utilized as a separate voltage divider with the VIN and VREF as shown with VOUT taken between the junction of the resistors. In this configuration the voltage output from the femur transducer is subtracted from the voltage output from the tibia transducer which resultant difference voltage may be employed as an output for the apparatus as will be explained.

Figure 5:
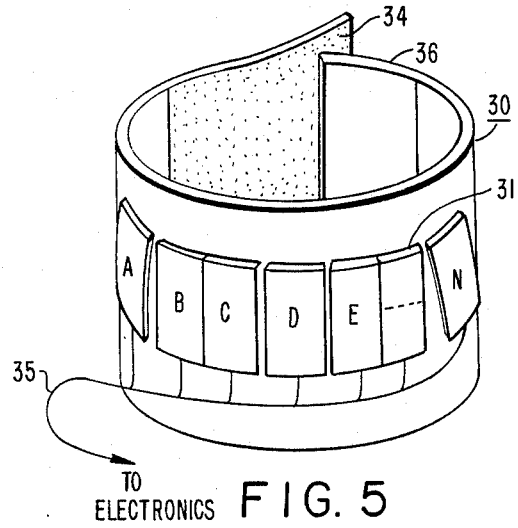
FIG. 5 is a knee band containing sensors which may be employed in this invention.

Referring to FIG. 5, there is shown a knee band 30 which essentially has a series of pockets as 31 designated as A to N indicating that there are a plurality of zones which are to be monitored to determine the correct alignment of the knee. Each pocket or zone will contain a transducer structure as shown in FIG. 2. The diaphragm devices may be inserted in each pocket or may be actually secured by glueing or bonding the diaphragm to the band 30 in a desired location by the technician or the physician in adjusting the device to the particular individual.

The output terminals of each of the diaphragms are directed into a common cable 35. The particular band may be secured to the user's knee by means of a Velcro straps as 34 and 36. It is, of course, understood that there are many types of bands which can be employed in this invention such as those including straps and so on as well as molded plastic members.

The band is secured to the user's knee such that the F and T sensors are located above and below the center of the knee band. In regard to this the technician will inform the user of how to emplace the band and indicate to the user the amount of tension necessary in accommodating the band to the knee. It is, of course, understood that the dimensions discussed in regard to the knee are relatively large, and hence there is room for error as it is only necessary that the transducers be positioned above and below so that they will respond to forces exerted on the femur and tibia as necessary.

In formulating the proper tabulated values, the technician can, of course, modify the position of the band within reason so that a range of proper values can be discerned. There are many techniques, for example, of monitoring knee motion which can be employed to develop the necessary values for providing a tabulation of correct operating conditions for the particular individual. These techniques involve x-ray techniques as well as various computer programs which will generate the data directly based on actual measurement values obtained from the individual who will use the apparatus.

Figure 6:
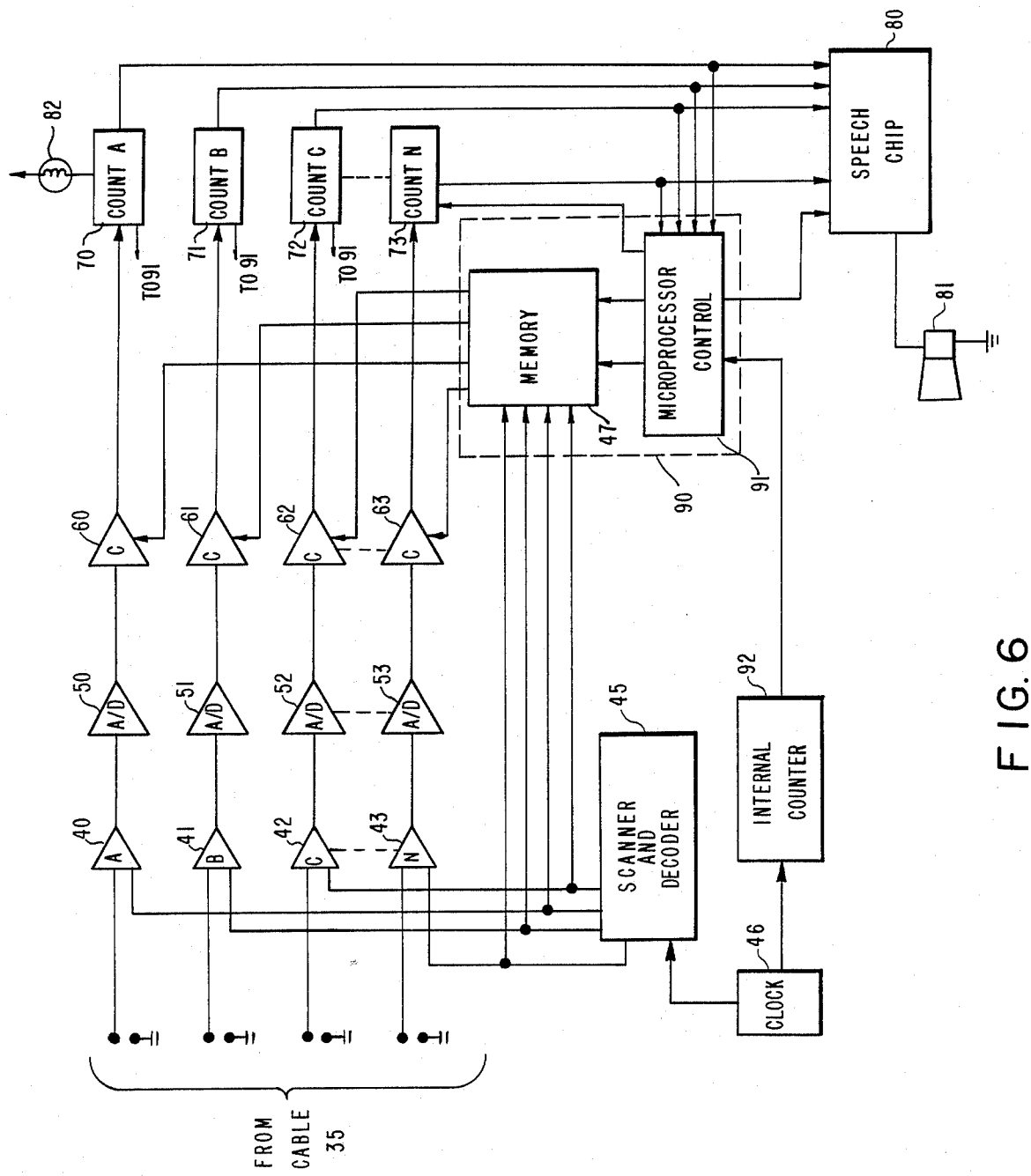
FIG. 6 is a detailed schematic depicting circuitry which is used in this invention.

Referring to FIG. 6, the outputs from cable 35 are directed to individual analog gates as 40, 41, 42, and 43. The gates are shown as four by way of example and are indicated by the zones A to N. Each gate has one lead which is the output voltage from the Wheatstone bridge array. Another input to each gate is supplied by a scanner 45. The scanner essentially is a digital counter including decoding gates and operates in synchronization with a clock 46 which steps the scanner to allow the scanner to enable each gate as 40 to 43 in sequence. Such scanners and decoders are well known in the art and are used in multiplexers. The output leads from each scanner are also coupled to the address inputs of a memory 47. In this manner the voltage output from each transducer is applied via its gate as gate 40 to analog-to-digital converter 50 which is associated with gate 40.

Accordingly, each gate as 41, 42, and 43 is associated with an analog-to-digital (A/D) converter as 51, 52 and 53. The analog-to-digital converter converts the analog output voltage coupled through the gate to a digital signal. This digital signal is applied to one input of a comparator as 60, 61, 62 and 63. The other output of the comparator is supplied by the memory which inputs the data stored therein according to the address furnished to the memory 46 by the scanner 45.

The memory has stored therein proper voltages for each zone as A to N which digital values were supplied by the physician or technician indicative of proper knee operation during a give knee exercise such as running in place, jumping and so on. The function of the comparators is to compare a proper digital signal as stored in the memory 47 with the actual signal developed by the user during exercise.

If this signal is exceeded, then there is an improper alignment of the knee in a given zone. The outputs of each comparator are further coupled to the input of respective counters as 70, 71, 72, and 73. The counters operate to advance a counter each time the comparator provides an output. Thus the counters 70 to 73 will count up to a predetermined value during a given time interval. Hence if a comparator such as 60 to 63 continues to provide an output during a number of scans, the counter will count up until it reaches a maximum count whereby it will send a signal to a speech chip device 80. Essentially, the speech chip is a conventional component and is a digital circuit which is capable of producing speech upon activation of a given input. Such chips are well known and are utilized in toys, learning devices, automobiles and so on and are operative to give audible commands to a user. The speech chip will then provide an audible indication via a speaker as 81 to inform the user that his knee joint has exceeded its limitations according to the particular zone which has been adversely affected.

This indication could be provided by means of a visual signal such as a lamp or light 82 which is coupled to the counter. The memory 47 may be part of a microprocessor 90 which has a microprocessor control 91 which is conventional in present technology. The microprocessor 91 can change the constants stored in memory as a function of the time interval that the exercise is being conducted. This time interval is monitored via clock 46 through an interval counter 92. The interval counter 92 is a conventional component and essentially provides a signal which monitors the time elapsed during the performance of the exercise. For example, the interval counter may produce a pulse each minute and the microprocessor will, therefore, change the memory contents every minute to thereby change the conditions sent to the comparators 60 to 63 during specified time intervals. This is necessary as the knee alignment problems may differ according to the length of time the exercise is performed.

Each counter as 70 to 73 has its output also coupled to the microprocessor control 91 in order to inform the microprocessor control that its maximum count has been reached so that the microprocessor can activate the speech chip 80 for the proper time interval necessary to give the user the required command. The microprocessor also has outputs coupled to the counters 70 to 73. These outputs can serve to reset the counters or to inhibit the counters when the maximum count is reached. In this manner, the microprocessor receives an indication from the counter that the maximum count has been reached and inhibits the counter from counting until the requisite signal has been transmitted by the speech chip 80.

In order to gain a clearer understanding of the system operation, the following description is believed to be warranted in conjunction with the above noted arrangement. In using the apparatus according to this invention, a technician or physician will emplace the knee band of FIG. 5 about the knee of the person to be tested. Based on the knowledge of his medical problem or potential problem, the technician will then connect the output leads from the sensors contained in the zone pockets of the knee band to a computer or to a voltage monitor. He will then instruct the user to undergo a particular exercise and record the optimum values of each zone sensed during the exercise. He will also record these values for selected time intervals during the exercise; as for example, at one, five or ten minute intervals.

This data is then tabulated for each zone and will constitute the information to be stored in the memory 47 or in the microprocessor 90. The number of sensors used and the orientation of the sensors with respect to the knee is selected by the technician or physician again according to the size, weight and nature of the injury or exercise prescribed for the individual.

Once the information is stored in memory and the sensors are placed in the proper position in the knee band, the user can now place the knee band as directed and commence the same exact exercise. Upon commencing the exercise, he will turn on the apparatus by flipping a switch which will power the sensors and energize the apparatus. The memory may be a magnetic disk or permanent storage memory which would be emplaced in the computer or microprocessor. Hence during the exercise, each sensor will be scanned by the apparatus in time sequence and the voltage output will be compared at the intervals with the data stored in the memory. The comparators will provide an output each time the voltage output as supplied by the sensors exceeds the stored output as prescribed or determined by the physician and stored in memory.

The counters as 70 to 73 are preset so that a given number of comparator outputs will indicate a faulty exercise mode. This is necessary as during knee exercise, one might exceed a required voltage one or more times which is relatively insignificant as a continuous excessive signal is determinative of a faulty alignment. Hence when a counter reaches its predetrmined count, it will energize the speech chip at a requisite output and also indicate this to the microprocessor control. Thus the microprocessor control will activate the speech chip to provide an actual audible warning to the user whereby the user will be informed that he is not performing the exercise correctly and hence will change or modify his actions.

The exercise can continue over a time interval as indicated and during predetermined intervals within the overall time, the data stored in the memory and to be compared may also vary. In this manner the user will be informed of whether he is performing the exercise correctly and will, therefore, modify the exercise according to these instructions. It is also noted that the microprocessor control, if receiving a counter input, will not update the data for the next interval and that is to allow the user to compensate for exercise according to the command received from the speech chip.

The particular apparatus can be utilized by runners or atheletes to which running or exercise is an essential part of the training regiment. The apparatus can also be used by persons who suffer from various types of joint diseases so that they can receive information regarding the proper alignment of the knee according to the above considerations.

As one can understand from the above description, there are many alternate ways of implementing the apparatus all of which are deemed to be encompassed within the spirit and scope of this invention.

For example, as seen in FIG. 6, the module 90 refers to the microprocessor which contains a memory. It is understood that the apparatus included in module 90 is contained in a computer such as a home computer, and hence the technician may supply the individual with a disk having all the pertinent data stored thereon for use with the apparatus. In this manner, each individual having a knee problem will obtain his own data pertinent to his own injuries and the particular knee band will accommodate only the necessary sensors indicative of the particular problem associated with the person's knee joint.

As should be clear from FIG. 6, the person will be informed as to a problem in each of the zones as A to N which are being monitored by the sensors, and therefore, the physician or technician can describe to the individual how the problem can be eliminated in regard to each zone by changing the method of performing the exercise. For example, if the person receives an indication that there is a violation of zone A, this may mean that he is his leg too high or it will relate to some other physical consequence in performing the exercise which the person can therefore control.

The apparatus depicted in FIG. 6 is extremely small as implemented by integrated circuits and hence the entire structue can be contained in a housing coupled to the knee band to provide the user his complete self-contained unit. It was also noted that various other types of sensors can be employed such as magnetic and other electrical sensors as well to monitor the relative motion of the knee and the alignment between the femur and the tibia.

I claim:

1. Apparatus for monitoring the proper alignment of a knee of a user, comprising:
   transducer means adapted to be coupled to the knee of said user and operative to provide an output signal indicative of the relative forces on the knee joint during an exercise, said transducer means including a first transducer section responsive mainly to forces exerted about the femur section of the knee, and a second transducer section responsive mainly to forces exerted about the tibia section of the knee, to provide said output signal proportional to the displacement of the tibia with respect to the femur,
   memory means for storing data indicative of predetermined force levels for said knee during said exercise,
   comparison means operative to compare data stored in the memory means with said output signal and for providing an indication signal when said output signal exceeds said stored force level data,
   means coupled to the comparison means for counting the indication signals provided by said comparison means, and
   means for issuing a warning signal when said counting means reaches a predetermined count.

2. The apparatus according to claim 1, wherein said transducer means comprises a variable resistance transducer having a first section adapted to be positioned on the knee of said user and operative to respond to forces exerted on the femur section of the knee of said user and a second section adapted to be positioned on the knee of said user and operative to respond to forces exerted on the tibia section of the knee of said user.

3. The apparatus according to claim 1, wherein said transducer means comprises a plurality of individual transducer means adapted to be placed on the knee of said user.

4. The apparatus according to claim 3, wherein said memory means contains a plurality of storage locations including respectively, in each of said locations, force level data for comparison with respective signals from individual transducer means.

5. The apparatus according to claim 4, further including scanning means coupled to said transducer and memory means for sequentially scanning each of said individual transducer means for simultaneously accessing force level data stored in a respective storage location.

6. The apparatus according to claim 5 wherein said means for issuing a warning signal comprises a speech generator.

7. The apparatus according to claim 6, wherein said transducer means are mounted on an adjustable band that is adapted to be supported on the knee of said user.

8. Apparatus for monitoring the proper alignment of a knee of a user, comprising:
   a plurality of transducer means adapted to be coupled to a knee of a user and placed about said knee for monitoring a plurality of zones of said knee and for providing a respective output signal indicative of the relative forces on each of said zones, respectively during movement of said knee, wherein each transducer means includes a first transducer section responsive mainly to forces exerted about the femur section of the knee, and a second transducer section responsive mainly to forces exerted about the tibia section of the knee, to provide an output signal proportional to the displacement of the tibia with respect to the femur in a respective zone,
   scanning means coupled to said transducer means and operative to sequentially scan said transducer means to sequence said output signals,
   memory means coupled to said scanning means and having stored therein in separate locations data indicative of a predetermined force level for each respective knee zone, wherein said memory means includes means coupled to said scanning means for outputting data from respective separate locations sequentially and simultaneously with the scanning of a respective individual transducer means,
   comparison means for comparing the output signal of each transducer means with the data stored in a respective memory location each time the transducer is scanned, and for outputting an indication when the output signal of the transducer exceeds the respective stored data,
   means for counting the indications from the comparison means for each transducer,
   warning means for issuing a warning when the number of indications counted for any transducer exceeds a predetermined count.

9. The apparatus according to claim 8, wherein said warning means provides an audible output informing said user of the zone.

10. The apparatus according to claim 8, wherein said memory means is a memory included in a microprocessor.

11. The apparatus according to claim 8, wherein said plurality of transducer means is supported on the surface of a knee band for encircling the knee of a user during knee movement.

12. The apparatus according to claim 8, wherein each of said transducer means includes a first variable resistance located in the first transducer section and a second variable resistance located in the second transducer section.

13. The apparatus according to claim 12, wherein said first and second variable resistances are coupled in a bridge array.

14. The apparatus according to claim 12, wherein said variable resistances are located on a common flexible diaphragm member, which member is flexible enough to follow knee movement.

15. A method of monitoring proper alignment of the knee joint of a user while engaged in exercise comprising the steps of:
   storing in a memory data indicative of a predetermined force level for a knee,
   detecting the level of force acting to displace the tibia and femur of the user during an exercise,
   comparing said detected level of force with said stored level of force,
   counting the number of times the detected level deviates from said stored level by a predetermined amount, and warning the user when the number counted exceeds a predetermined amount.

16. The method according to claim 15, wherein the step of detecting includes the step of placing a variable resistance transducer on said knee.

17. The method according to claim 15, further including the step of changing said data stored in said memory according to elapsed time intervals during the course of said exercise.

18. The method according to claim 15, wherein the step of warning includes providing an audible indication.

* * * * *